United States Patent [19]
Hiejima et al.

[11] Patent Number: 5,839,470
[45] Date of Patent: Nov. 24, 1998

[54] THREE-WAY STOPCOCK AND FLOW RATE CONTROL DEVICE IN USE THEREOF

[75] Inventors: Katsuhiro Hiejima; Yosuke Naoki, both of Ohtsu, Japan

[73] Assignee: Nissho Corporation, Osaka, Japan

[21] Appl. No.: 832,510

[22] Filed: Apr. 3, 1997

[30] Foreign Application Priority Data

Apr. 10, 1996 [JP] Japan .................................. 8-088183

[51] Int. Cl.⁶ .................................................. F16K 11/08
[52] U.S. Cl. ................................... 137/599; 137/625.47
[58] Field of Search ............................... 137/625.47, 599

[56] References Cited

U.S. PATENT DOCUMENTS

| | | | |
|---|---|---|---|
| 3,769,975 | 11/1973 | Nimoy et al. | 128/214.4 |
| 4,314,586 | 2/1982 | Folkman | 137/625.47 |
| 4,349,022 | 9/1982 | Ishikawa | 128/214 R |
| 4,644,967 | 2/1987 | Wyatt et al. | 137/599 |
| 4,840,613 | 6/1989 | Balbierz | 604/51 |
| 5,501,674 | 3/1996 | Trombley, III et al. | 604/247 |

FOREIGN PATENT DOCUMENTS

| | | |
|---|---|---|
| 0 008 451 A1 | 3/1980 | European Pat. Off. . |
| 0 314 470 A2 | 5/1989 | European Pat. Off. . |
| 2 279 570 | 1/1995 | United Kingdom . |

*Primary Examiner*—John Fox
*Attorney, Agent, or Firm*—Kubovcik & Kubovcik

[57] ABSTRACT

A three-way stopcock and a flow rate control device having a flow rate control unit for controlling the flow rate by flow resistances of flow rate control tubes. The three-way stopcock includes a plug portion in a cylindrical shape having a liquid path in a T-like shape, a cylindrical portion having two flow inlet ports and one flow outlet port, into which the plug portion can be inserted rotatably and in a liquid tight fit, and a switch lever capable of attachably and detachably engaging with the plug portion, wherein when the liquid path of the plug portion communicates with the flow outlet portion of the cylindrical portion by rotation of the plug portion by the switching lever, the liquid path of the plug portion communicates with at least one of the two flow inlet ports of the cylindrical portion.

3 Claims, 5 Drawing Sheets

THREE-WAY STOPCOCK AND FLOW RATE CONTROL DEVICE IN USE THEREOF

BACKGROUND OF THE INVENTION

1. Field of the Invention

The present invention relates to a three-way stopcock and to a flow rate control device using the stopcock. More particularly, the present invention relates to a three-way stopcock capable of switching in several stages the flow rate of a liquid medicine and to a flow rate control device where the three-way stopcock is integrated with a flow control unit thereof. The flow rate control device is preferably used by being connected to a ballooned liquid medicine continuous injector (an injector where liquid medicine is filled in a balloon made of an elastic rubber material and liquid medicine is continuously injected over a period of many hours into blood vessels or the like by utilizing the force produced by contraction of the balloon) that is used as a means for administering a liquid analgesic, anesthetic, antibiotic, or carcinostatic agent into blood vessels, hypodermic portions, epidural portions or the like continuously in a small amount.

2. Description of Related Art

A three-way stopcock has conventionally been used in the medical field when a blood transfusion or a solution transfusion is carried out.

A three-way stopcock is typically constituted by a cylindrical portion having three branch tubes projecting in a T-like shape at the outer periphery of the cylindrical portion, a plug portion inserted in and rotatably attached to the cylindrical portion and having a liquid path in a T-like shape corresponding to the branch tubes of the cylindrical portion, and a lever attached to the plug portion for switching the flow path. The lever is integrally formed with the plug portion or fixed to the plug portion.

When such a three-way stopcock is used as a flow path switching means of a liquid medicine injector, since the switching means has a structure where anyone can easily rotate the lever, a patient per se can switch routes of the liquid medicine. Therefore, there is a fear that the injection of liquid medicine will intentionally be finished earlier than prescribed or that the ratio of the mixture of liquid medicines will be changed at the patient's own discretion. Further, there is a fear of switching the lever when a patient accidentally presses the stopcock by tossing about in bed. There have been actual reports of, in the case of a general solution transfusion (raw food, glucose, Ringer's solution), etc., a patient intentionally increasing the number of intravenous drips by operating a clamp, or a clamp being disengaged by vibration or timing whereby liquid medicine is rapidly injected.

When such a situation occurs while a liquid solution comprising a powerful drug such as an opioid, peptide, carcinostatic agent or the like is being injected, the influence on the patient is enormous.

Meanwhile, with respect to a variable small flow rate control device used in a ballooned liquid medicine continuous injector, a device comprising flow rate control tubes connected to a multi-way stopcock has already been proposed (Japanese Unexamined Patent Publication No. JP-A-5-84310). The device is constituted by a main body having a cylindrical valve chamber where one flow inlet port and at least three flow outlet ports are formed. A plug having a cylindrical valve portion is rotatably inserted into the valve chamber of the main body, in which a slit opened in a fan-like shape and slender holes in a straight tube shape extending opposely in the radial direction from the base of the slit, are formed at the valve portion and, even if the slender holes of the valve portion are connected to any of the flow outlet ports, the slit is connected to the flow inlet port.

However, according to the above-described flow rate control device, one flow rate control tube is necessary for each flow outlet port and various sizes of the flow rate control tubes are necessary. It is troublesome in view of production control and assembly operation to fabricate various sizes of flow rate control tubes and integrate them simultaneously. Also, the use thereof involves a drawback where the switch angle of the lever is decreased for a large number of switchings and the display is complicated whereby erroneous operation is liable to occur.

The present invention has been achieved as a result of an intensive study in view of the above-described situation and it is an object of the present invention to provide a flow rate control device where switching of liquid medicine routes by a patient is difficult. Also, it is an object of the present invention to provide a flow rate control device of a multi-stage switching type where the operation of switching flow paths is simple and erroneous operation rarely occurs.

SUMMARY OF THE INVENTION

The inventors have conceived as a result of the intensive study that the object of making it difficult for a patient to switch liquid medicine routes is resolved by adopting as a means of switching the flow path of a flow rate control device a three-way stopcock in which a lever is separated from a plug portion and is attachably and detachably engaged with the plug portion. Furthermore, the inventors have conceived that the object of simplifying the flow path switching operation and preventing erroneous operation, is fulfilled by pertinently integrating the three-way stopcock with a flow rate control unit of a flow rate control device.

Accordingly, there is provided attachably and detachably a three-way stopcock attachably and detachably which makes it difficult for a patient to switch liquid medicine routes of a flow rate control device, and which is useful as a means for switching flow paths of a flow rate control device. The three-way stopcock is constituted by a plug portion having a cylindrical shape and in which is provided a liquid path in a T-like shape, a cylindrical portion having two flow inlet ports and one flow outlet port, into which the plug portion can be rotatably inserted and in a liquid tight fit, and a switch lever capable of attachably and detachably engaging with the plug portion, wherein when the liquid path of the plug portion communicates with the flow outlet portion of the cylindrical portion by rotating the plug portion by the switching lever, the liquid path of the plug portion communicates with at least one of the two flow inlet ports of the cylindrical portion.

Moreover, in order to simplify the flow path switching operation and preventing the occurrence of erroneous operation, there is provided a flow rate control device having a flow rate control unit for controlling the flow rate of a liquid by flow resistances of a plurality of flow rate control tubes provided therein and which includes the three-way stopcock. Three branch paths are provided on a flow inlet port side of the flow rate control unit, each of the flow rate control tubes being connected at a first end thereof to one of the branch paths; two branch paths are provided on a flow outlet port side of the flow rate control unit, one of the flow rate control tubes is connected at a second end thereof to one of the two branch paths, a connection tube is connected at a first end thereof to the flow-outlet port of the three-way stopcock and at a second end thereof to the other of the two branch paths; and each of the two remaining flow rate control tubes is respectively connected to each of the two flow inlet ports of the three-way stopcock. The flow rate control unit may be incorporated in a housing and a through hole for inserting the switch lever may be provided at a position of the housing corresponding to the plug portion of the there-way stopcock whereby the switch lever can be engaged with the plug portion.

DETAILED DESCRIPTION OF THE PREFERRED EMBODIMENTS

Embodiments of the present invention are explained below in reference to the drawings.

Figure 1:
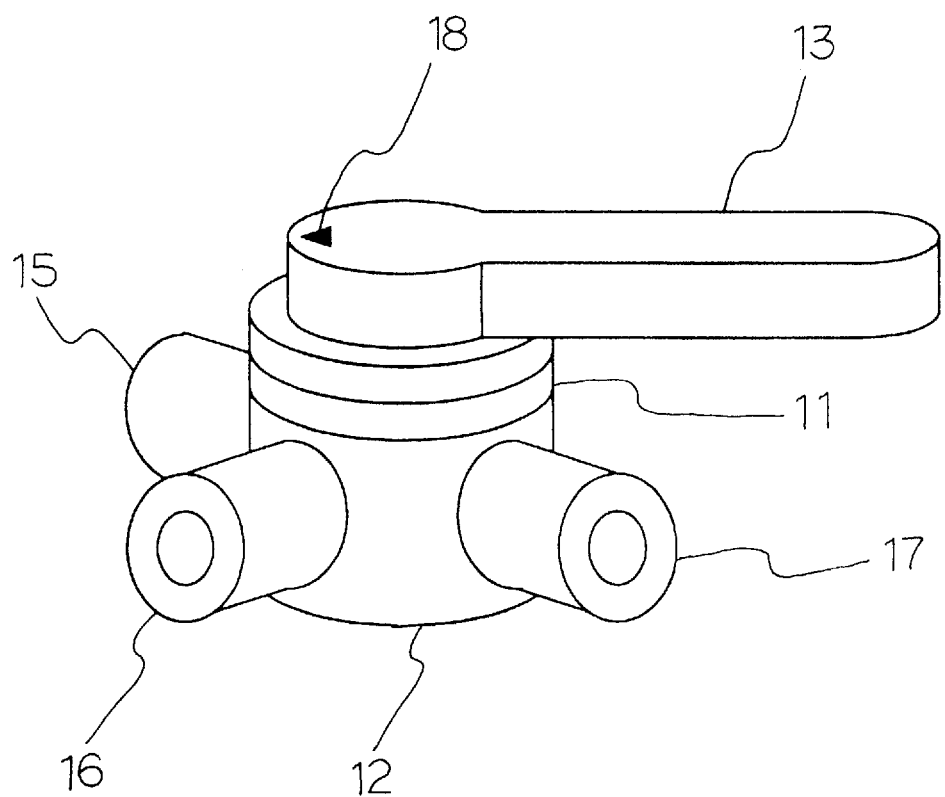
FIG. 1 is a perspective view showing an embodiment of a three-way stopcock according to the present invention.

As shown in FIG. 1, a three-way stopcock 1 in accordance with a first aspect of the present invention, is constituted by a plug portion 11 having a cylindrical shape, a cylindrical portion 12 into which the plug portion 11 can be inserted rotatably and in a liquid tight fit, and a switch lever 13 capable of engaging attachably and detachably with the plug portion 11.

Figure 2:
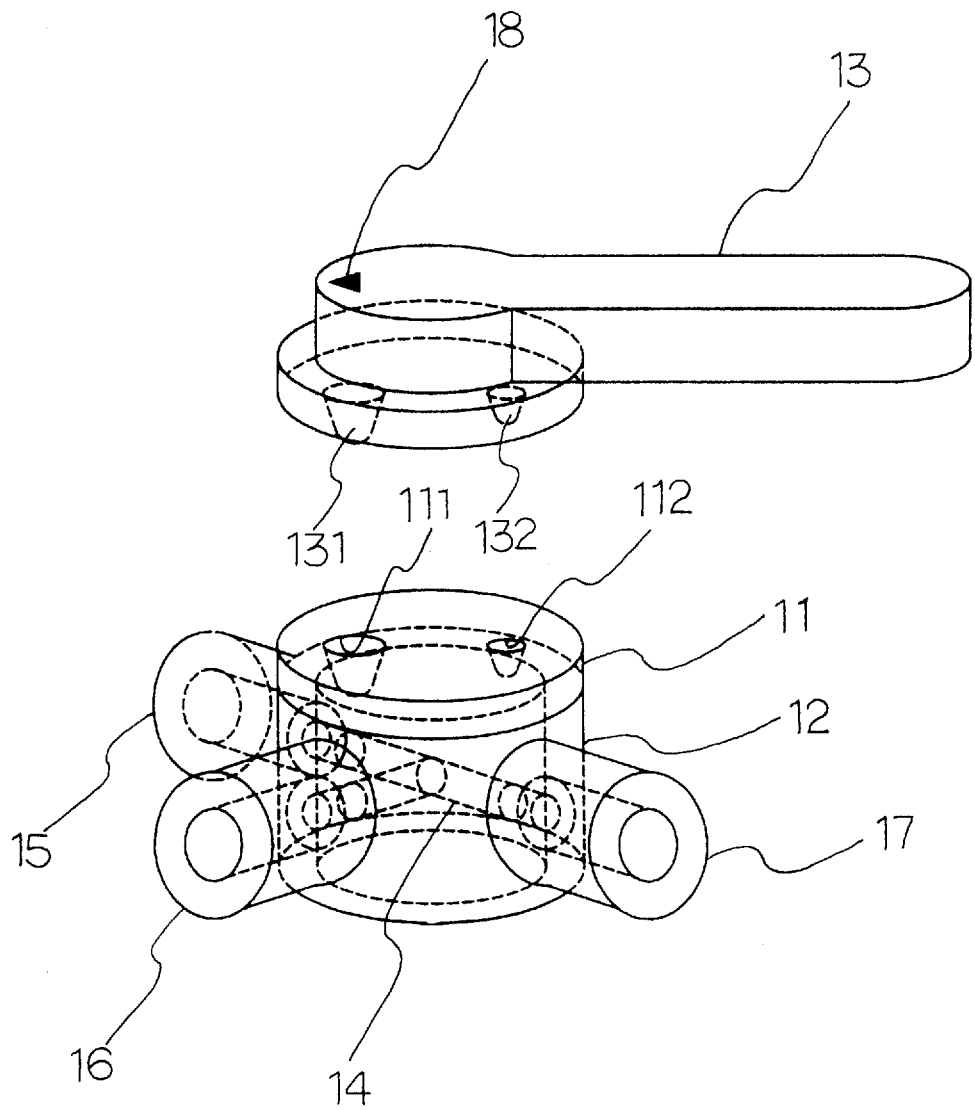
FIG. 2 is an exploded explanatory view of FIG. 1.

As shown in FIG. 2, a liquid path 14 in a T-like shape is formed in the plug portion 11. Meanwhile, two flow inlet ports 15 and 16 and one flow outlet port 17 are formed in the cylindrical portion 12. When the liquid flow path 14 of the plug portion 11 communicates with the flow outlet port 17 of the cylindrical portion 12 by rotating the plug portion 11 by the switching lever 13, the liquid path 4 of the plug portion 11 communicates with at least one of the flow inlet ports 15 and 16 of the cylindrical portion 12. The switch lever 13 is provided with at least two engaging projections 131 and 132, which engage attachably and detachably with engaging recesses 111 and 112 provided on the top face of the plug portion 11 to correspond with the engaging projections 131 and 132. An arrow mark 18 or the like may be provided at the front end of the switch lever 13 for facilitating the engagement of the engaging projections 131 and 132 with the engaging recesses 111 and 112. Further, with respect to an engagement between the plug portion 11 and the switch lever 13, engaging projections (not illustrated) may be provided on the plug portion 11 and engaging recesses (not illustrated) may be provided in the switch lever 13.

Figure 3:
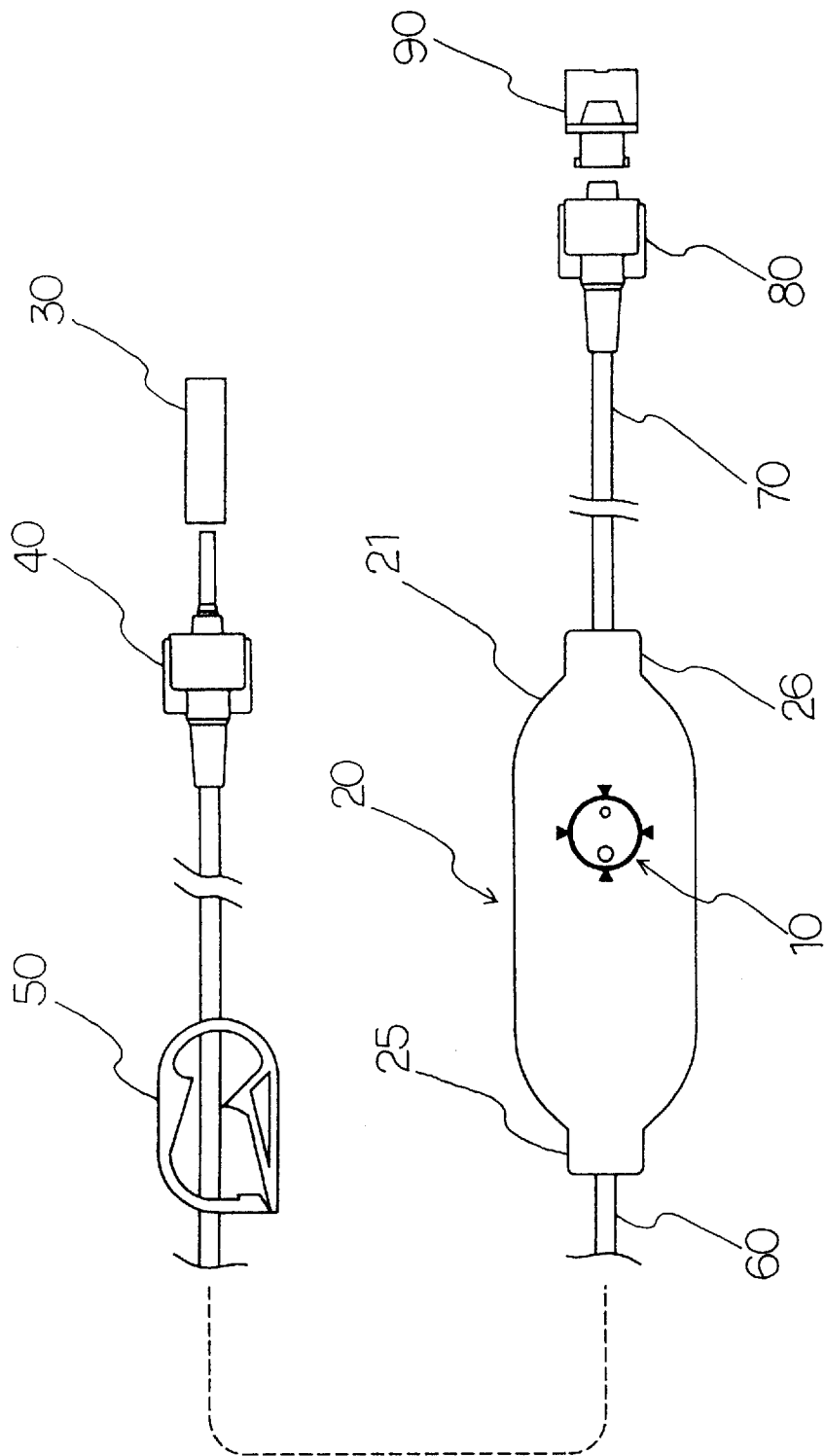
FIG. 3 is a plane view showing a flow rate control device of the present invention in which the three-way stopcock of FIG. 1 is integrated.
Figure 4:
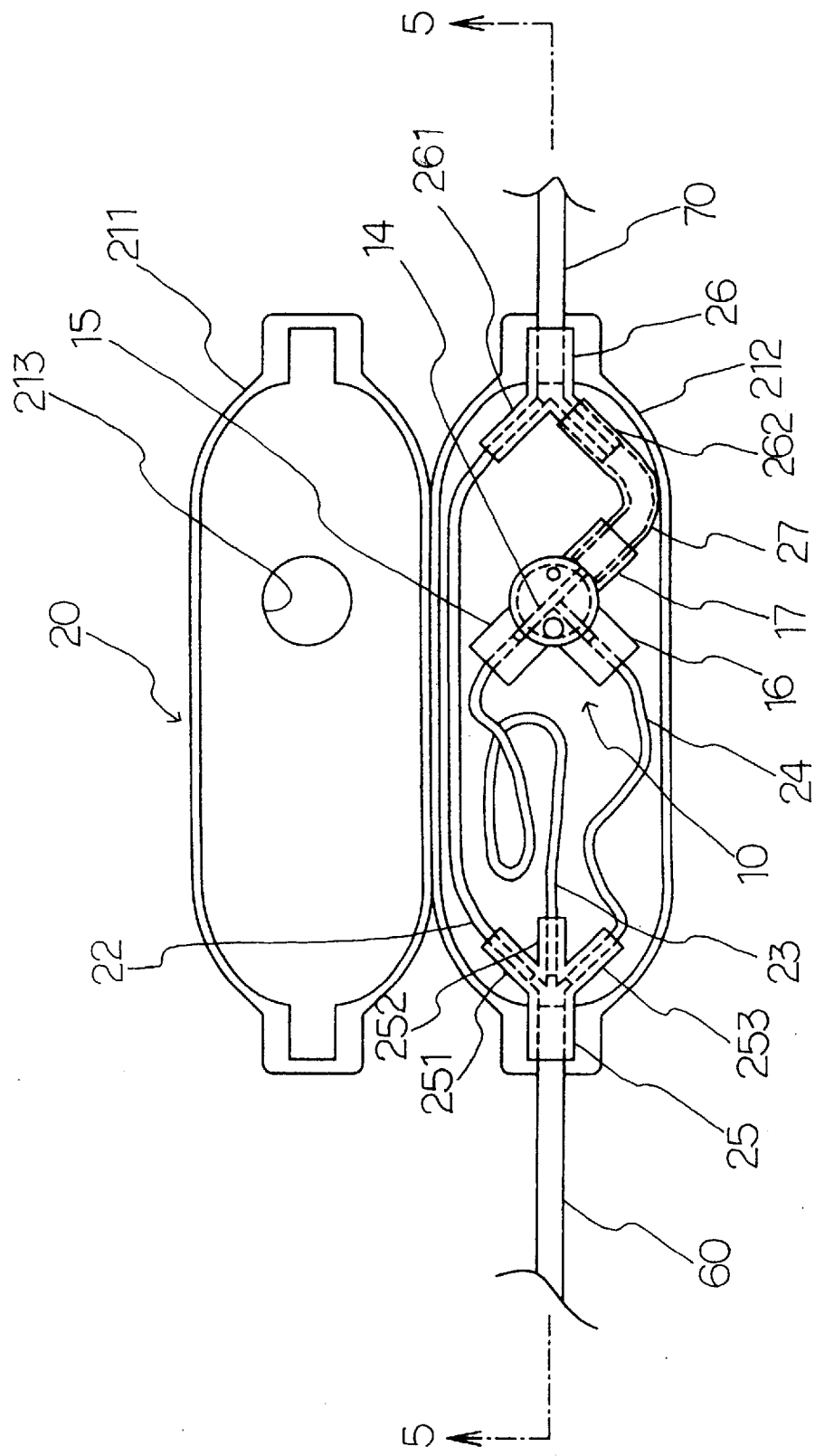
FIG. 4 is a plane view showing a state of the device where a lid of a housing of the flow rate control unit of the flow rate control device of FIG. 3 is opened.
Figure 5:
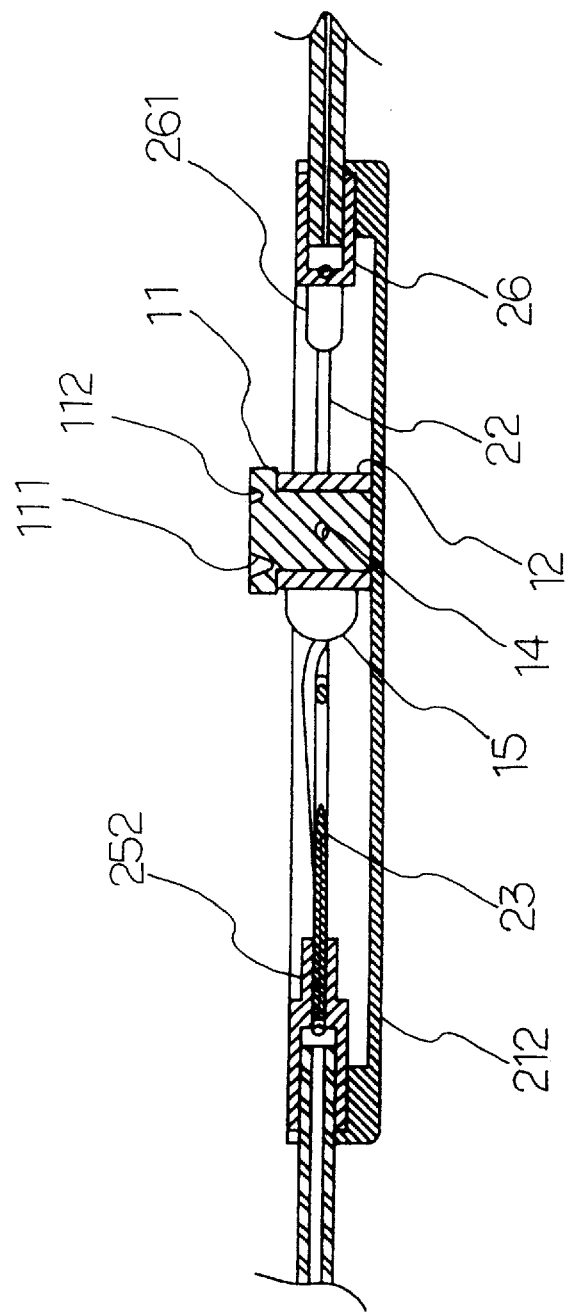
FIG. 5 is an enlarged sectional view taken along line 5—5 of FIG. 4.

In a flow rate control device in accordance with a second aspect of the present invention, as shown in FIG. 3 through FIG. 5, there is provided a flow rate control device having a flow rate control unit 20 where the flow rate is controlled by flow resistances of flow rate control tubes 22, 23 and 24, and wherein the three-way stopcock 10 according to the first aspect of the present invention is integrated into the flow rate control unit 20 and the flow rate can be switched in multi stages by the three-way stopcock 10.

As shown in FIG. 3, the flow rate control device is generally constituted by the flow rate control unit 20, a connection tube 60 connected to an inlet 25 of the flow rate control unit 20, a connection tube 70 connected to an outlet 26 of the flow rate control unit 20, a connector 40 attached to the front end of the connection tube 60 and a clamp 50 provided midway in the tube as necessary. Also, a connector 80 is attached to the front end of the connection tube 70. Incidentally, in FIG. 3 numerals 30 and 90 designate caps of the connectors 40 and 80, respectively.

As shown, for example, in FIGS. 4 and 5, in the flow rate control unit 20, three branch paths 251, 252 and 253 are installed on the side of the inlet 25 and the flow rate control tubes 22, 23 and 24 are connected, respectively, to the branch paths 251, 252 and 253. Meanwhile, two branch paths 261 and 262 are provided on the side of the outlet 26 of the flow rate control unit 20, the flow rate control tube 22 is connected to one branch path 261 and a connection tube 27 is connected to the other branch path 262. Further, the flow rate control tubes 23 and 24 are respectively connected to the flow inlet ports 15 and 16 of the three-way stopcock 10 and the connection tube 27 is connected to the flow outlet port 17 of the three-way stopcock 10.

The flow rate control unit 20 is preferably incorporated in a housing 21 comprising a lid 211 and a main body 212 as illustrated in FIG. 4. A through hole 213 is provided at a position of the lid 211 corresponding to the plug portion 11 of the three-way stopcock to provide for insertion of the switch lever 13 and engaging of the lever with the plug portion 11. In using the flow rate control device, the switch lever 13 is inserted through the through hole 213, the switch lever 13 is engaged with the plug portion 11 of the three-way stopcock 10 and the switch lever 13 is rotated whereby desired flow rate settings can be obtained.

An explanation will be given of setting of flow rates as follows.

Four kinds of flow rate settings are feasible by using various combinations of the flow rate control tubes 22, 23 and 24 in FIG. 4.

For example, assuming the flow rates of the flow rate control tubes 22, 23 and 24, respectively, to be 1 ml/hr, 1 ml/hr and 2 ml/hr, since, according to the state shown in FIG. 4 the flow rate control tubes 23 and 24 communicate with the flow outlet port 17 via the liquid path 14, the flow rate at the outlet 26 is 4 ml/hr which is the sum of the flow rate of the flow rate control tube 22 communicating with the outlet 26 and the flow rates of the flow rate control tubes 23 and 24. When the plug portion 11 is rotated 90° in the clockwise direction, since the liquid path 14 does not communicate with the flow outlet port 17, the flow rate at the outlet 26 is 1 ml/hr, that is, the flow rate of only the flow rate control tube 22. When the plug portion 11 is rotated further by 90° in the clockwise direction, the flow rate control tube 23 communicates with the flow outlet port 17 via the liquid path 14 and, therefore, the flow rate at the outlet 26 is 2 ml/hr as a sum of the flow rates of the flow rate control tubes 22 and 23. When the plug portion 11 is rotated still further by 90° in the clockwise direction, the flow rate control tube 24 communicates with the flow outlet port 17 via the liquid path 14 and accordingly, the flow rate at the outlet 26 is 3 ml/hr as a sum of the flow rates of the flow rate control tubes 22 and 24.

Table 1 indicates examples of flow rate settings by using the flow rate control device illustrated in FIG. 4, including the above-described combinations. Additionally, further various flow rate settings are naturally feasible by integrating two or more of the three-way stopcocks 10 according to the first aspect of the present invention in the flow rate control unit 20 of the flow rate control device.

TABLE 1

| Flow rate of flow rate control tube (ml/hr) | | Combinations of flow rate control tubes | | | |
|---|---|---|---|---|---|
| | | 22 | 22 + 23 | 22 + 24 | 22 + 23 + 24 |
| Flow rate control tubes | 22:1 23:1 24:2 | 1 | 2 | 3 | 4 |
| Flow rate control tubes | 22:2 23:1 24:2 | 2 | 3 | 4 | 5 |
| Flow rate control tubes | 22:3 23:1 24:2 | 3 | 4 | 5 | 6 |

As apparent from the above-described explanation, the following effects can be achieved by adopting the flow rate control device of the present invention.

(1) The switch lever of the three-way stopcock is attachable and detachable and the switching of the flow paths is carried out by engaging the switch lever with the plug portion of the three-way stopcock and, therefore, it is difficult for a patient per se to switch the flow rate.

(2) The three-way stopcock is incorporated in the housing and the through hole 213 is provided at a position of the lid 211 corresponding to the plug portion 11 of the three-way stopcock 10 for inserting the switch lever 13 and engaging it with the plug portion 11 and, accordingly, the flow path is not switched by an accident such as dropping or pressing the flow control device or the like.

(3) Switching of the various flow rates is feasible by turning angles of 90° and various combinations of the flow rate control tubes and the three-way stopcock and, therefore, the flow rate switching operation is simplified and erroneous operation rarely occurs if the flow rate display is indicated on the housing.

What is claimed is:

1. A flow rate control device comprising a flow rate control unit wherein a liquid flow rate is controlled by flow resistances of flow control tubes provided therein, said flow rate control unit comprising:

a flow inlet port having an inlet and three branch outlet paths;

a flow outlet port having an outlet and two branch inlet paths;

a three-way stopcock comprising a cylindrical plug portion having a T-shape flow path provided therein which opens into the side of said cylindrical plug;

a cylindrical housing portion having two flow inlet ports and one flow outlet port and in which the plug portion is rotatably inserted in a liquid tight fit; and a switch lever capable of attachably and detachably engaging with the plug portion;

wherein said T-shape flow path of said cylindrical plug portion is arranged so as to communicate with said flow outlet port and flow inlet ports of said cylindrical housing when said cylindrical plug portion is rotated by means of said switch lever and wherein when an opening of said T-shape flow path is aligned with said flow outlet port at least one other opening of said T-shape flow path is aligned with a flow inlet port of said cylindrical housing;

three flow rate control tubes, each connected at a first end thereof to one of each of said three branch outlet paths of said flow inlet port, one of said flow rate control tubes connected at a second end thereof to one of said two branch inlet paths of said flow outlet port and each of the remaining two flow rate control tubes connected at a second end thereof to each of said flow inlets of said three-way stopcock; and a connection tube connected at a first end thereof to said flow outlet of said three-way stopcock and at a second end thereof to the other of said two branch inlet paths;

wherein a fluid delivered to said flow inlet port of said flow rate control unit flows through the flow rate control tube connected to a branch outlet path of said flow inlet port to said flow outlet port and flows through none, one or both of said remaining two flow rate control tubes connected to said three-way stopcock and to said flow outlet port according to the position of said T-shape flow path.

2. The flow rate control device according to claim 1, wherein the flow rate control unit is incorporated in a housing and a through hole for inserting said switch lever is provided at a position of the housing corresponding to the position of the plug portion of the three-way stopcock whereby the switch lever and the plug portion can be engaged with each other.

3. The flow rate control device according to claim 2 wherein the resistance to flow of at least one of said flow rate control tubes is different from the resistance to flow of at least one other of said flow rate control tubes.

* * * * *